United States Patent
Sun et al.

(10) Patent No.: US 6,517,236 B2
(45) Date of Patent: Feb. 11, 2003

(54) METHOD AND APPARATUS FOR AUTOMATED THERMAL IMAGING OF COMBUSTOR LINERS AND OTHER PRODUCTS

(75) Inventors: Jiangang Sun, Westmont, IL (US); William A. Ellingson, Naperville, IL (US); Chris M. Deemer, Evanston, IL (US)

(73) Assignee: The University of Chicago, Chicago, IL (US)

( * ) Notice: Subject to any disclaimer, the term of this patent is extended or adjusted under 35 U.S.C. 154(b) by 6 days.

(21) Appl. No.: 09/784,597

(22) Filed: Feb. 15, 2001

(65) Prior Publication Data

US 2002/0110176 A1 Aug. 15, 2002

(51) Int. Cl.$^7$ ............................. G01N 25/72; G01J 5/00
(52) U.S. Cl. ............................. 374/4; 374/5; 374/124; 250/341.6
(58) Field of Search ............................. 374/5–7, 45, 50, 374/124, 4, 153, 137, 120, 121, 130; 250/341.6, 332, 442.11

(56) References Cited

U.S. PATENT DOCUMENTS

| | | | |
|---|---|---|---|
| 4,126,033 A | * 11/1978 | Bartoli et al. | 73/15 A |
| 4,632,561 A | * 12/1986 | Rosencwaig et al. | 356/432 |
| 4,803,358 A | * 2/1989 | Kato et al. | 250/310 |
| 4,965,451 A | * 10/1990 | Solter | 250/330 |
| 5,504,366 A | * 4/1996 | Weiss et al. | 73/863 |
| 5,711,603 A | 1/1998 | Ringermacher et al. | |
| 6,000,844 A | * 12/1999 | Cramer et al. | 374/5 |
| 6,273,603 B1 | * 8/2001 | Cheindline et al. | 374/43 |
| 6,343,874 B1 | * 2/2002 | Legrandjacques et al. | 374/5 |

FOREIGN PATENT DOCUMENTS

| | | | |
|---|---|---|---|
| JP | 409236755 A | * 9/1997 | G02B/21/24 |

OTHER PUBLICATIONS

"Front Flash Thermal Imaging Characterization of Continuous Fiber Ceramic Composites" by C. Deemer, J.G.Sun, W.A.Ellingson, and S. Short, 23rd Annual Cocoa Beach Int. Conf. On Engineering Ceramics and Structures, Jan. 25–29, 1999.

"Early Time Pulse Echo Thermal Wave Imaging" by Han et al., Review of Progress in Quantitative Nondestructive Evaluation, vol. 15, pp. 519–524, 1996.

"Nondestructive Evaluation of Materials by Infrared Thermography" by X. Maldague, Springer–Verlag, London, 1993.

"Pulse phase infrared thermography" by X. Maldague et al., J. Appl. Phys., 79(5), pp. 2694–2698, 1996.

Flash Method of Determining Thermal Diffusivity, heat capacity, and Thermal Conductivity, by Parker et al., J. Appl. Phys., 32:1679–1684, 1861.

Thermal Imaging Measurement and Correlation of Thermal Diffusivity in Continuous Fiber, by J.G. Sun et al., Thermal Conductivity 24, eds, P.S. Gaal and D.E. Apostolescu, pp. 616–622, 1999.

* cited by examiner

Primary Examiner—Christopher W. Fulton
Assistant Examiner—Gail Verbitsky
(74) Attorney, Agent, or Firm—Joan Pennington

(57) ABSTRACT

A method and apparatus are provided for automated nondestructive evaluation (NDE) thermal imaging tests of combustor liners and other products. The apparatus for automated NDE thermal imaging testing of a sample includes a flash lamp positioned at a first side of the sample. An infrared camera is positioned near a second side of the sample. A linear positioning system supports the sample. A data acquisition and processing computer is coupled to the flash lamp for triggering the flash lamp. The data acquisition and processing computer is coupled to the infrared camera for acquiring and processing image data. The data acquisition and processing computer is coupled to the linear positioning system for positioning the sample for sequentially acquiring image data.

6 Claims, 5 Drawing Sheets

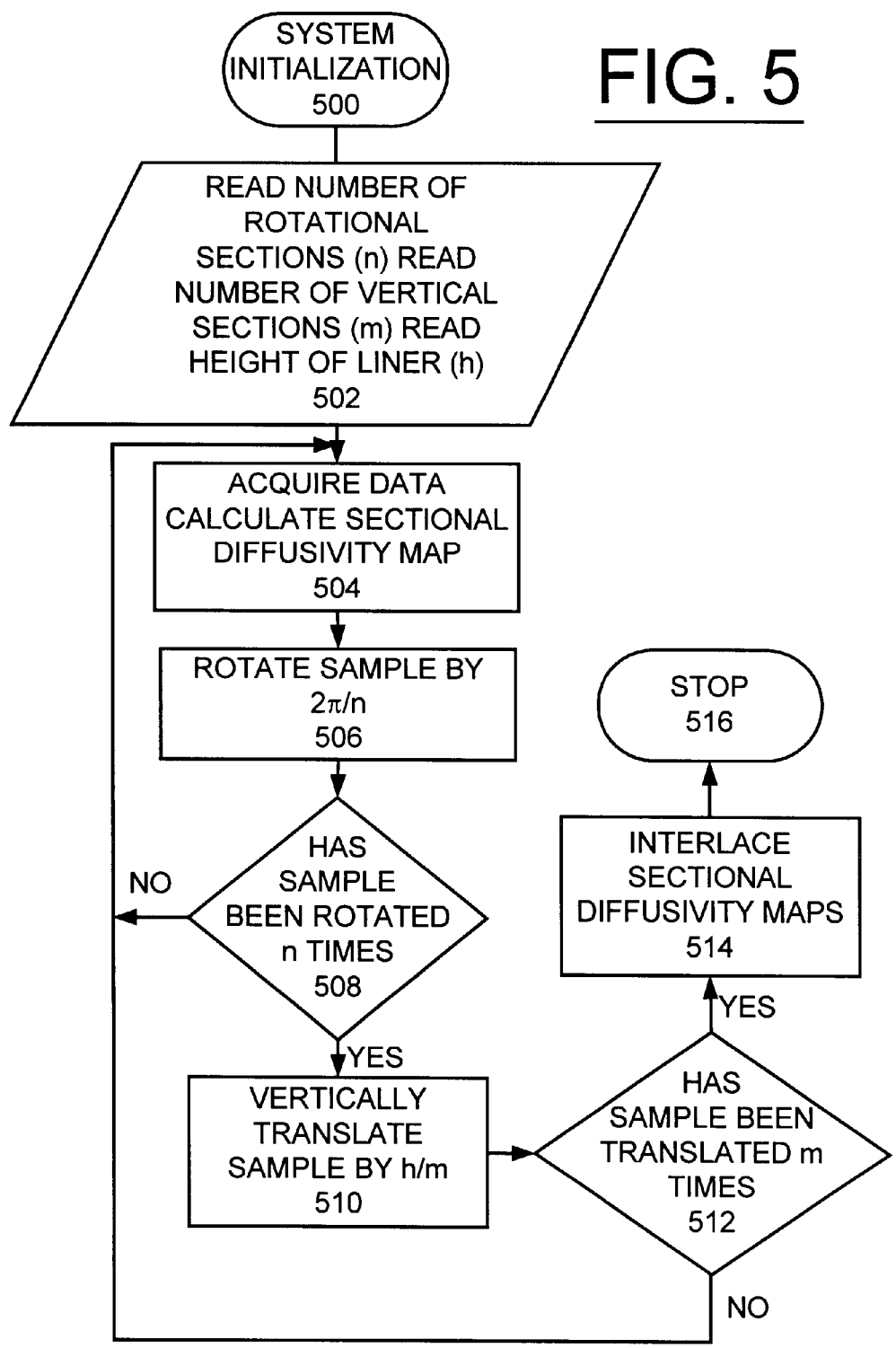

METHOD AND APPARATUS FOR AUTOMATED THERMAL IMAGING OF COMBUSTOR LINERS AND OTHER PRODUCTS

The United States Government has rights in this invention pursuant to Contract No. W-31-109-ENG-38 between the United States Government and Argonne National Laboratory.

FIELD OF THE INVENTION

The present invention relates to a method and apparatus for automated thermal imaging of combustor liners and other products; and more particularly, to a method and apparatus for automated non-destructive evaluation (NDE) thermal imaging tests of combustor liners and other products.

DESCRIPTION OF THE RELATED ART

Combustor liners are made at a high cost and are used in severe environments. An advanced ceramic matrix composite (CMC) liner is the single most important structural component expected to be widely used in land and air based heat engines. Because of their high costs, considerable effort has been devoted to characterization during processing to produce defect free components, as well as intermittently during engine operation to assess their lifetimes. Current non-destructive evaluation (NDE) testing is conducted in the laboratory with all testing steps conducted manually. The entire process is very time consuming and sometimes inaccurate, for example, due to misalignment resulting from manual positioning. Combustor liner characterization is critical for manufacturers to improve processing technique. Also combustor liner characterization is important to assess liner lifetime.

Non-destructive testing using transient thermography which relies upon the transfer of heat through an object over a period of time is known in the art. For example, U.S. Pat. No. 5,711,603, issued Jan. 27, 1998 to Ringermacher et al. and entitled "NONDESTRUCTIVE TESTING:TRANSIENT DEPTH THERMOGRAPHY" discloses a non-destructive testing technique and system using transient depth thermography.

In known testing arrangements, all steps in the testing are conducted manually, including positioning of the test sample, data acquisition, and data compilation. As a result, considerable time is required for completion of the testing. Also misalignment problems often occur in such manual testing arrangements.

A principal object of the present invention is to provide a method and apparatus for automated non-destructive evaluation (NDE) thermal imaging tests of combustor liners and other products.

It is another object of the invention to provide such method and apparatus for automated non-destructive evaluation (NDE) thermal imaging tests of combustor liners and other products that is fully automated, generally fast, and accurate.

It is another object of the invention to provide such method and apparatus for automated non-destructive evaluation (NDE) thermal imaging tests of combustor liners and other products that is fully automated and acquires complete combustor liner data without human intervention.

It is another object of the invention to provide such method and apparatus for automated non-destructive evaluation (NDE) thermal imaging tests of combustor liners and other products substantially without negative effect and that overcome many of the disadvantages of prior arrangements.

SUMMARY OF THE INVENTION

In brief, a method and apparatus are provided for automated non-destructive evaluation (NDE) thermal imaging tests of combustor liners and other products. The apparatus for automated NDE thermal imaging testing of a sample includes a flash lamp positioned at a first side of the sample. An infrared camera is positioned near a second side of the sample. A linear positioning system supports the sample. A data acquisition and processing computer is coupled to the flash lamp for triggering the flash lamp. The data acquisition and processing computer is coupled to the infrared camera for acquiring and processing image data. The data acquisition and processing computer is coupled to the linear positioning system for positioning the sample for sequentially acquiring image data.

BRIEF DESCRIPTION OF THE DRAWINGS

The present invention together with the above and other objects and advantages may best be understood from the following detailed description of the preferred embodiments of the invention illustrated in the drawings, wherein:

FIG. 5 is a flow chart illustrating exemplary steps of a method for NDE testing of combustor liner in accordance with the preferred embodiment.

DETAILED DESCRIPTION OF THE PREFERRED EMBODIMENTS

Figure 1:
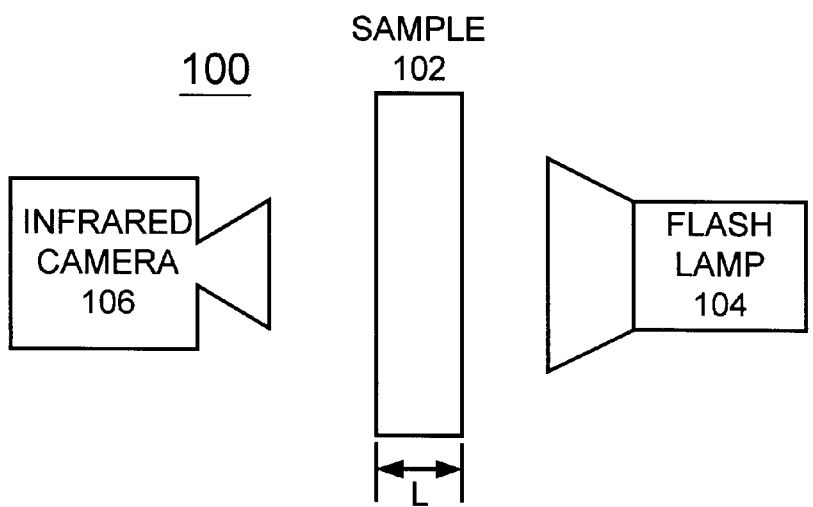
FIG. 1 is a diagram illustrating an experimental setup for measuring through-thickness thermal diffusivity image of a test sample.

Having reference now to the drawings, in FIG. 1 there is shown an experimental setup apparatus generally designated by the reference character 100 for measuring through-thickness thermal diffusivity image of a test sample 102. Experimental setup apparatus 100 includes a flash lamp 104 for providing a pulse of thermal energy for heating a thin layer of material on a first surface, such as the back surface. Experimental setup apparatus 100 includes an infrared camera 106. The temperature rise at the a second, opposed surface or the front surface of the test sample 102 is continuously monitored by the infrared camera 106 that takes a series of infrared-thermal images to be stored in a computer for further processing. For example, infrared camera 106 sees an area represented by 256×256 pixels. After the flash provided by flash lamp 104, infrared camera 106 takes a series of images, such as, for example, 50–500 frames.

Infrared thermal imaging is used to measure the full-field distribution through established correlations with known simulated defects in samples having the same thermal diffusivity values. Thermal diffusivity is a material property related to the transient heat transfer speed in the material. A defect such as a crack is a material discontinuity. The crack gap is filled with air and therefore alters, typically reducing heat transfer speed through the material. Advantages of thermal imaging technique include the ability to measure full-field thermal diffusivity distribution, an important thermal property for these materials, and the high sensitivity in detecting defects.

Figure 2:
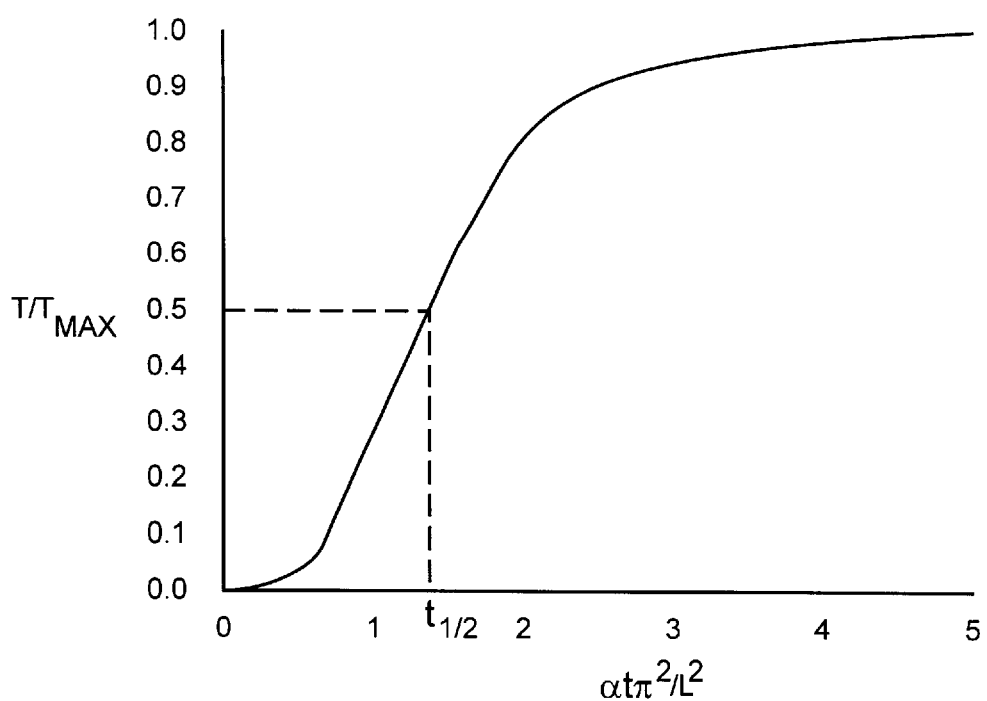
FIG. 2 is a chart illustrating a normalized temperature-time curve at typical point on a front surface of a test-sample with an impulse thermal energy applied to a back surface at time t=0.

Referring also to FIG. 2, the speed of the temperature rise at each pixel of the camera array is determined by a characteristic time, for example, the half-rise time, $t_{1/2}$, which represents the time when the temperature rises to one-half of the maximum temperature rise, $T_{max}$. FIG. 2 shows a normalized theoretical temperature/time curve at one point on the front surface of the test sample 102. The through-thickness thermal diffusivity at this pixel, α, is then determined as follows:

$$\alpha = (0.139 L^2)/t_{1/2} \quad (1)$$

Where L is the thickness of the planar sample 102. By calculating the thermal diffusivity at each pixel of the camera array and then constructing a thermal diffusivity image or map, we can infer the existence and the size, shape, and severity of defects from the thermal diffusivity image.

Figure 3:
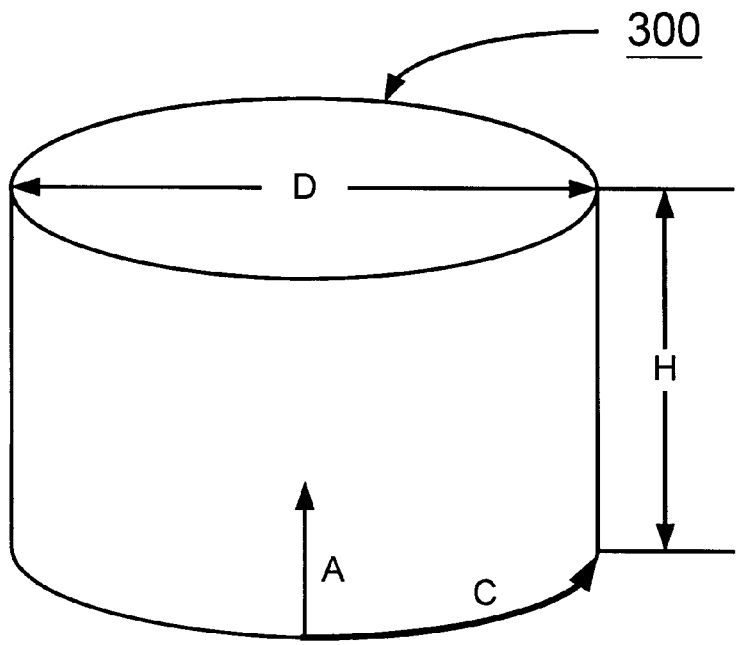
FIG. 3 is a diagram illustrating a combustor liner.

Referring to FIG. 3, there is shown a diagram illustrating a combustor liner 300 having a diameter indicated by an arrow labeled D and a height indicated by an arrow labeled H. An axial direction is indicated by an arrow labeled A and a circumferential direction is indicated by an arrow labeled C. Consider, for example, a combustor liner 300 having a diameter D of 8 inches and a height H of 8 inches, and being 0.15 inch thick and made of advanced ceramic matrix composite (CMC). With an infrared camera 106 consisting of 256×256 pixels, infrared sensors, each converting the observed infrared energy in a particular wavelength range, such as, for example 3–5 μm to a digital signal that is related to the intensity of the infrared energy, which is further related to the surface temperature at that pixel, infrared camera 106 can be normalized so that the output signals of all 256×256 infrared sensors are correlated linearly with the temperature of the viewed surface. High frame-rate operation of infrared camera 106 is critical in evaluating advanced ceramic matrix composite (CMC) components due to their high thermal diffusivities. Infrared camera 106 can take images at a high frame rate, for example, greater than 120 frames per second with the full array of 256×256 infrared sensors at a temperature resolution of less than 0.015° C. When testing with pulsed thermal imaging, the thermal transient time is usually very short, less than 0.5s, and this must be resolved by the infrared camera 106 in order to determine an accurate half-rise time.

During a flash thermal imaging test, one section or area of a sample surface is examined at a time. After the thermal impulse from the flash lamp 104 is applied, a series of thermal images, for example 100 frames is taken by the infrared camera 106 and stored in a computer (not shown in FIG. 1). These images represent the time history of the temperature change on the front surface of the sample 102. The through-thickness thermal diffusivity data or map for this section is then determined from equation 1 for every pixel in the image array. To cover the entire sample surface, conventionally the sample is manually translated, either rotationally or linearly, or both.

Surface dimensions seen by the infrared camera 106 determine the spatial resolution of the thermal diffusivity image. If the infrared camera 106 is focused on a surface area of 4-inch by 4-inch square, for example, the spatial resolution represented by each pixel in the image is 0.156-inch×0.156-inch square with 4 inches divided by 256 sensors in each dimension, or 0.4-mm×0.4-mm square. Defects larger than this spatial resolution may be visually detected from the image data. For the combustor liner 300 shown in FIG. 3, image data would include 2 rows and 8 columns of 4-inch×4-inch sectional images. For a 30 inch diameter and 8 inch long combustor liner 300, a typical measurement of its full-field thermal diffusivity requires taking 2 rows and 28 columns of 4-inch by 4-inch square sectional images. A complete image of the combustor liner 300 is then compiled from these sectional images.

Figure 4:
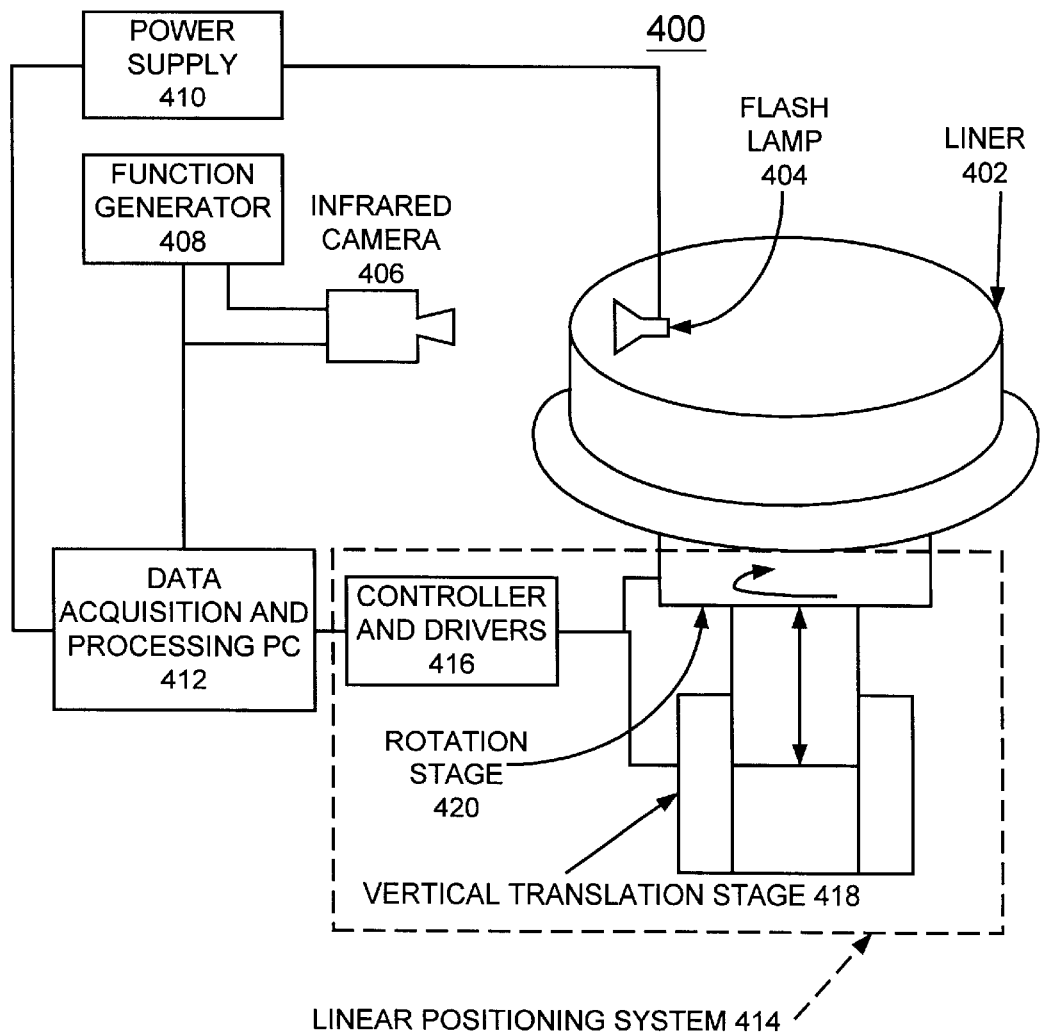
FIG. 4 is a diagram illustrating an automated thermal imaging apparatus for NDE testing of combustor liner in accordance with the preferred embodiment.

Referring to FIG. 4, there is shown an automated thermal imaging system for NDE testing of a combustor liner 402 in accordance with the preferred embodiment and generally designated by the reference character 400. Automated thermal imaging system 400 performs a thermal imaging method of the preferred embodiment that is a non-contact, non-immersion, high-resolution and high-sensitivity NDE technique for liner characterization. Automated thermal imaging system 400 is portable and can be easily set up at laboratories, component processing plants, or engine operating sites.

Automated thermal imaging system 400 includes a flash lamp 404 for providing a pulse of thermal energy for heating a first surface, such as the back surface of the combustor liner 402. Automated thermal imaging system 400 includes a high-resolution and high-sensitivity infrared camera 406 with 256×256 pixel focal plane array of infrared sensors. A function generator 408 coupled to the infrared camera 406 to control the infrared camera and a power supply 410 associated with the flash lamp 404 are operatively controlled by a data acquisition and processing personal computer 412.

Automated thermal imaging system 400 includes a linear positioning system 414 including a controller and drivers unit 416 coupled to the data acquisition and processing personal computer 412 for operatively controlling a vertical translation stage 418 and a rotation stage 420. Automated thermal imaging system 400 provides accurate positioning and automated stage motion control with the vertical translation stage 418 and rotation stage 420. Automated thermal imaging system 400 automatically compiles the entire line image using data processing software for full 256×256 pixel image processing in about 10–20 seconds.

During operation of the automated thermal imaging system 400, first the combustor liner 402 is placed on the rotation stage 420 and vertical translation stage 418. The infrared camera 406 is placed outside the liner and focused on a section of the outside surface of the combustor liner 402. The flash lamp 404 is positioned inside the combustor liner 402 and faces the section viewed by the infrared camera 406. Then the control program performed by the data acquisition and processing personal computer 412 is initiated. The control program triggers the flash lamp 404 and acquires a series of thermal images with the infrared camera 406 and performs calculations to obtain thermal diffusivity data for the current section. Then the liner is moved in predetermined directions, circumferential, vertical or both with the infrared camera 406 distanced to view the adjacent section for the next data acquisition. The control program of the preferred embodiment automatically allows the process to continue until the entire surface of the combustor liner 402 has been tested. The control program compiles a complete image data of the combustor liner 402 from all sectional image data according to the sequence that the sectional image data was obtained. For a typical 30-inch diameter, 8-inch lone liner 404 with 4-inch×4-inch sections for a total of 54 sections, complete testing takes less than one hour.

FIG. 5 illustrates exemplary method steps performed by the automated thermal imaging system 400 for NDE testing of the combustor liner 402 in accordance with the preferred embodiment. System initialization is performed as indicated in a block 500. Next the number of rotational section (n), the number of vertical sections (m) and the height of liner (h) are read as indicated in a block 502. Image data is acquired and sectional diffusivity map is calculated as indicated in a block 504. Next the combustor liner 402 is rotated by $2\pi/n$ as indicated in a block 506. Checking whether the sample combustor liner 402 has been rotated n times is performed as indicated in a decision block 508. If not, then the sequential operations return to block 504 and image data is acquired and sectional diffusivity map is calculated. When determined at decision block 508 that the sample combustor liner 402 has been rotated n times, then the sample combustor liner 402 is vertically translated by h/m as indicated in a block 510. Checking whether the sample combustor liner 402 has been vertically translated m times is performed as indicated in a decision block 512. If not, then the sequential operations return to block 504 and image data is acquired and sectional diffusivity map is calculated. When determined at decision block 512 that the sample combustor liner 402 has been vertically translated m times, the sectional diffusivity maps are interlaced as indicated in a block 514. This completes the sequential operations as indicated in a block 516.

While the present invention has been described with reference to the details of the embodiments of the invention shown in the drawing, these details are not intended to limit the scope of the invention as claimed in the appended claims.

What is claimed is:

1. A method for automated non-destructive evaluation (NDE) thermal imaging testing of a sample including combustor liners comprising the steps of:

providing a flash lamp positioned at a first side of the sample;

providing an infrared camera positioned near a second side of the sample;

providing a linear positioning system supporting the sample; said linear positioning system including a vertical translation stage for vertically translating the sample and a rotation stage for rotating the sample; and a controller and drivers unit for operatively controlling said vertical translation stage and said rotation stage;

utilizing a data acquisition and processing computer for performing the steps of;

triggering said flash lamp, acquiring and processing image data from said infrared camera;

sequentially positioning the sample with said linear positioning system for sequentially acquiring sectional image data of the sample including the steps of rotating the sample a predetermined number of times; and vertically translating the sample a predetermined number of times.

2. A method for automated non-destructive evaluation (NDE) thermal imaging testing of a sample including combustor liners as recited in claim 1 further includes the step of compiling a complete image data of the sample.

3. A method for automated non-destructive evaluation (NDE) thermal imaging testing of a sample including combustor liners as recited in claim 2 wherein the step of compiling a complete image data of the sample includes the step of interlacing a plurality of sectional diffusivity maps.

4. A method for automated non-destructive evaluation (NDE) thermal imaging testing of a sample including combustor liners as recited in claim 1 wherein the step of acquiring and processing image data from said infrared camera includes the step of acquiring image data for an array of 256×256 infrared sensors from said infrared camera.

5. A method for automated non-destructive evaluation (NDE) thermal imaging testing of a sample including combustor liners as recited in claim 2 wherein the step of acquiring and processing image data from said infrared camera includes the steps of acquiring a series of said image data for said array of 256×256 infrared sensors from said infrared camera.

6. A method for automated non-destructive evaluation (NDE) thermal imaging testing of a sample including combustor liners as recited in claim 5 wherein the step of acquiring and processing image data from said infrared camera includes the step of calculating a thermal diffusivity data map for each of said array of 256×256 infrared sensors from said infrared camera.

* * * * *